(12) United States Patent
Busch et al.

(10) Patent No.: US 7,181,969 B2
(45) Date of Patent: Feb. 27, 2007

(54) ULTRASONIC TEST CHAMBER FOR TRAY PRODUCTION SYSTEM AND THE LIKE

(75) Inventors: Ralph E. Busch, Olney, MD (US); Brandon D. Fallon, Reston, VA (US); James C. McKeon, Woodbridge, VA (US)

(73) Assignee: Sonix, Inc., Springfield, VA (US)

( * ) Notice: Subject to any disclaimer, the term of this patent is extended or adjusted under 35 U.S.C. 154(b) by 0 days.

(21) Appl. No.: 10/387,881

(22) Filed: Mar. 13, 2003

(65) Prior Publication Data

US 2004/0011133 A1 Jan. 22, 2004

Related U.S. Application Data

(60) Provisional application No. 60/396,347, filed on Jul. 16, 2002.

(51) Int. Cl.
G01N 29/00 (2006.01)

(52) U.S. Cl. .......................... 73/618; 73/644
(58) Field of Classification Search ................ 73/618, 73/622, 633, 644, 861.39, 861.41, 661, 620, 73/629, 627, 600, 41.2, 45.5; 367/140, 171; 134/73, 108, 184
See application file for complete search history.

(56) References Cited

U.S. PATENT DOCUMENTS

| | | | |
|---|---|---|---|
| 3,063,290 A | 11/1962 | Kaserman et al. | |
| 3,489,608 A | 1/1970 | Jacobs et al. | |
| 3,558,093 A | 1/1971 | Bok | |
| 3,617,045 A | 11/1971 | DaCosta et al. | |
| 3,678,735 A | 7/1972 | Boulanger et al. | |
| 3,737,573 A | 6/1973 | Kessler | |
| 3,760,822 A | 9/1973 | Evans | |
| 3,765,431 A | 10/1973 | Jannett et al. | |
| 3,790,281 A | 2/1974 | Kessler et al. | |
| 3,850,025 A | 11/1974 | Nakanishi et al. | |
| 3,850,027 A | 11/1974 | Nakanishi et al. | |
| 3,886,739 A | 6/1975 | Cramer et al. | |
| 3,886,793 A | 6/1975 | Cramer et al. | |
| 3,898,839 A | 8/1975 | White | |
| 3,988,196 A | 10/1976 | Wanesky | |
| 4,008,602 A | 2/1977 | Love | |
| 4,012,951 A | 3/1977 | Kessler | |
| 4,058,000 A | 11/1977 | Ries et al. | |
| 4,164,150 A | 8/1979 | Ries et al. | |
| 4,208,915 A | 6/1980 | Edwards | |
| 4,238,962 A | 12/1980 | Taenzer | |
| 4,252,125 A | 2/1981 | Iinuma | |
| 4,316,271 A * | 2/1982 | Evert | 367/140 |
| 4,332,016 A | 5/1982 | Berntsen | |
| 4,344,448 A * | 8/1982 | Potts | 134/73 |
| 4,472,975 A | 9/1984 | Beck et al. | |
| 4,517,985 A * | 5/1985 | Teslawski et al. | 600/446 |

(Continued)

*Primary Examiner*—Hezron Williams
*Assistant Examiner*—Jacques Saint-Surin (57) ABSTRACT

A method and apparatus for ultrasonic inspection of one or more objects in an object holder. In a first embodiment of the method, the objects are immersed in a tank containing coupling fluid and a flow of fluid is generated in the tank beneath the object holder, thereby producing a suction pressure that tends to hold the objects in the holder. Each object is insonified with ultrasound from an ultrasonic transducer and the ultrasound reflected from or transmitted through the object is sensed. In a further embodiment, the object to be inspected is moved between the upper and lower chambers of a scanning station, over a surface in the lower chamber. A coupling fluid is supplied to the upper chamber so that coupling fluid flows through one or more holes in the bottom of the upper chamber and fills the space between the ultrasound emitting surface of the ultrasonic transducer and the object to be scanned, thereby providing coupling for the ultrasound and tending the hold the objects in the object holder.

48 Claims, 5 Drawing Sheets

U.S. PATENT DOCUMENTS

| | | | |
|---|---|---|---|
| 4,518,992 A | | 5/1985 | Kessler et al. |
| 4,526,038 A | * | 7/1985 | Box et al. .................... 73/644 |
| 4,543,130 A | | 9/1985 | Shwartzman |
| 4,662,215 A | | 5/1987 | Eckert |
| 4,781,067 A | | 11/1988 | Cichanski |
| 4,807,634 A | * | 2/1989 | Enjoji et al. ................ 600/437 |
| 4,854,337 A | | 8/1989 | Bunkenburg et al. |
| 4,866,986 A | | 9/1989 | Cichanski |
| 4,920,803 A | | 5/1990 | Karaki et al. |
| 4,924,707 A | | 5/1990 | Kliesch |
| 4,977,779 A | | 12/1990 | Karaki et al. |
| 5,014,711 A | | 5/1991 | Nagasaki |
| 5,060,517 A | | 10/1991 | Fushimi et al. |
| 5,077,695 A | | 12/1991 | Khuri-Yakub et al. |
| 5,117,697 A | | 6/1992 | Takishita et al. |
| 5,195,729 A | | 3/1993 | Thomas et al. |
| 5,212,987 A | | 5/1993 | Dransfeld et al. |
| 5,240,522 A | | 8/1993 | Tanaka et al. |
| 5,301,552 A | | 4/1994 | Nagura et al. |
| 5,320,225 A | | 6/1994 | Kirkpatrick |
| 5,359,895 A | | 11/1994 | Isenberg et al. |
| 5,374,021 A | | 12/1994 | Kleinman |
| 5,374,829 A | | 12/1994 | Sakamoto et al. |
| 5,431,054 A | | 7/1995 | Reeves et al. |
| 5,469,742 A | | 11/1995 | Lee et al. |
| 5,531,119 A | * | 7/1996 | Meyers ........................ 73/661 |
| 5,585,564 A | | 12/1996 | Brunty et al. |
| 5,600,068 A | | 2/1997 | Kessler et al. |
| 5,629,865 A | | 5/1997 | Roth |
| 5,646,351 A | | 7/1997 | Good et al. |
| 5,668,452 A | | 9/1997 | Villarreal et al. |
| 5,684,252 A | * | 11/1997 | Kessler et al. ................ 73/618 |
| 5,874,319 A | | 2/1999 | Dunaway et al. |
| 5,922,961 A | | 7/1999 | Hsu et al. |
| 5,948,985 A | * | 9/1999 | Brautigan et al. ............ 73/622 |
| 5,996,415 A | | 12/1999 | Stanke et al. |
| 6,027,605 A | | 2/2000 | Lehmann et al. |
| 6,062,084 A | | 5/2000 | Chang et al. |
| 6,085,591 A | | 7/2000 | Mallard |
| 6,089,095 A | | 7/2000 | Yang et al. |
| 6,227,946 B1 | | 5/2001 | Gonzalez-Martin et al. |
| 6,230,896 B1 | | 5/2001 | Lambert |
| 6,261,370 B1 | | 7/2001 | Otsuki et al. |
| 6,357,136 B1 | * | 3/2002 | Erickson et al. |
| 6,460,414 B1 | | 10/2002 | Erickson et al. |
| 6,513,796 B2 | | 2/2003 | Leidy et al. |
| 6,524,351 B2 | | 2/2003 | Ohta |
| 6,540,014 B2 | | 4/2003 | Getchel et al. |
| 6,554,003 B1 | * | 4/2003 | Birang et al. ................ 134/1.3 |
| 6,603,103 B1 | | 8/2003 | Ulrich et al. |
| 6,709,877 B2 | | 3/2004 | Tsui et al. |
| 6,712,765 B2 | | 3/2004 | Glenn |
| 6,743,296 B2 | | 6/2004 | Kao |
| 6,880,387 B2 | | 4/2005 | Kessler et al. |
| 6,890,302 B2 | | 5/2005 | Oravecz et al. |
| 6,895,820 B2 | | 5/2005 | Oravecz et al. |
| 6,912,908 B2 | * | 7/2005 | Kessler et al. ................ 73/620 |
| 6,921,672 B2 | | 7/2005 | Satya et al. |

* cited by examiner

ULTRASONIC TEST CHAMBER FOR TRAY PRODUCTION SYSTEM AND THE LIKE

RIGHT OF PRIORITY

This application claims priority to and benefit of earlier filing date of U.S. Provisional Application No. 60/396,347, filed Jul. 16, 2002, the content of which is incorporated herein by reference.

FIELD OF THE INVENTION

This invention relates generally to the field of ultrasonic testing. More particularly, this invention relates to a system and method for ultrasonic inspection of objects supported by an object holder.

BACKGROUND OF THE INVENTION

Non-destructive inspection of parts has been used for many years. More recently, ultrasonic inspection has been extended to small parts such as integrated circuits or other electronic components. During the manufacture of Integrated circuits, the parts are often loosely arranged in trays or holders to facilitate transfer of the parts through the production process. In order to prevent delays in the production process, an ultrasonic tester that can accommodate trays of parts is required.

An ultrasonic tester may include three sections. The first section is a de-bubbling area where the parts in the carriers are wetted and air bubbles are removed. The normal convention is to submerge the parts and 'wiggle' them to remove the air bubbles. The second section is a scanning station where wetted and bubble free parts are ultrasonically scanned. In order to complete the scan in a short time, the ultrasonic transducer must be moved across the parts at high speed in close proximity to the parts. The result is a motion in the fluid that tends to move the parts in the carriers or dislodge them from the carrier. The third section is a drying area, where a gas stream is used to dry any residual coupling fluid from the parts. Typically compressed and/or heated air is directed across the parts. Each of these processes tends to dislodge the parts when they are loosely arranged in a tray or carrier.

BRIEF DESCRIPTION OF THE DRAWINGS

The features of the invention believed to be novel are set forth with particularity in the appended claims. The invention itself however, both as to organization and method of operation, together with objects and advantages thereof, may be best understood by reference to the following detailed description of the invention, which describes certain exemplary embodiments of the invention, taken in conjunction with the accompanying drawings in which:

DETAILED DESCRIPTION OF THE INVENTION

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the description below, like reference numerals are used to describe the same, similar or corresponding parts in the several views of the drawings.

One aspect of the present invention is a method and a system for ultrasonic scanning of parts in which coupling fluid is used to hold parts in a parts holder or tray. A further aspect of the invention is method and system for holding parts in a parts holder while bubbles are removed from parts before they are scanned. Still further aspects of the invention will be apparent from the following detailed description of illustrative embodiments.

Figure 1:
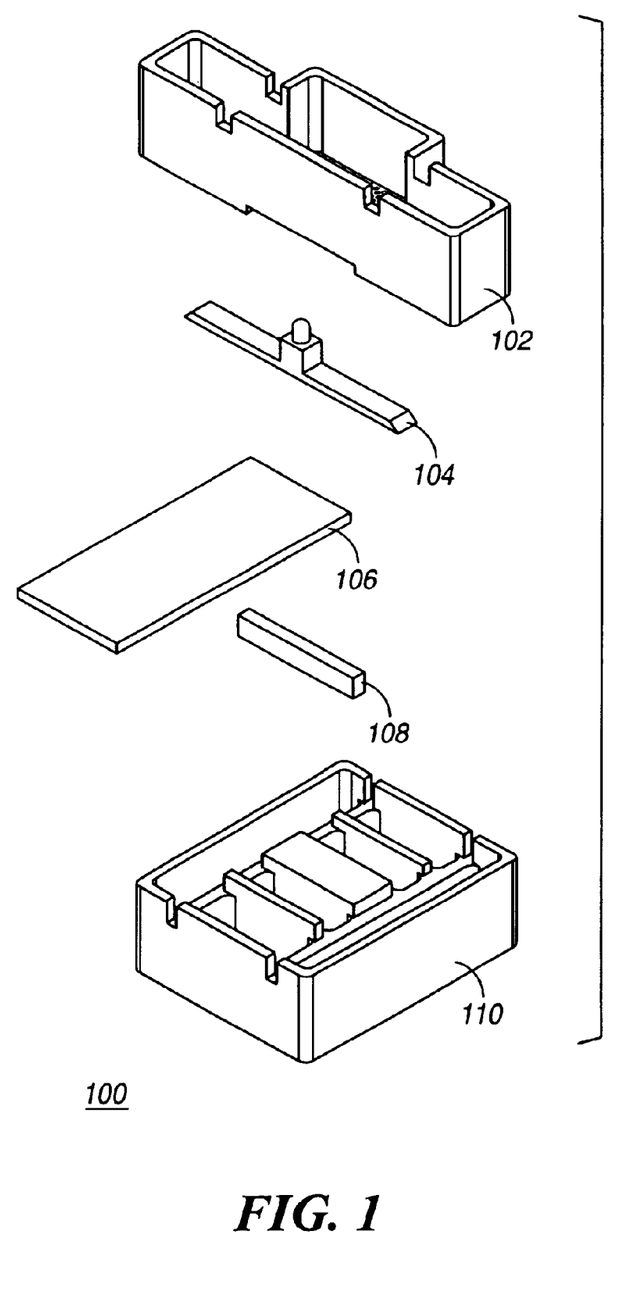
FIG. 1 is an exploded view of an ultrasonic test chamber in accordance with certain embodiments of the present invention.

In one embodiment, the ultrasonic test chamber of the present invention includes three functional sections: a de-bubbling station, a scanning station and a dryer. FIG. 1 shows an exploded view of an exemplary test chamber 100 in accordance with the invention. The test chamber comprises a lower chamber 110 and an upper chamber 102. The chambers held by a frame or housing (not shown) so that the gap between the two chambers may be adjusted to accommodate trays of varying thickness. In this embodiment, the lower chamber is fixed and the upper chamber may be raised or lowered. The upper chamber houses a moveable plate or scanning bar 104, the bottom of which is flush with the bottom of the upper chamber. A first ultrasonic transducer is mounted in the scanning bar and can be independently moved up or down (relative to the lower chamber and relative to the scanning bar) to place the transducer at the proper distance from the parts. During operation, a parts tray 106 is passed beneath the transducer and plate. A second ultrasonic transducer 108 may be mounted in the lower chamber 110 beneath the tray of parts 106, so that transmission of ultrasound through the parts may be measured. The first or second transducers may, for example, comprise a single element transducer having a spot, line or flat focus, an array of transducers, one or more array transducers or a combination thereof. The arrays may be line arrays having a single dimension, or area arrays having two dimensions. Example transducers include the Panametrics V313 crystal transducer, the Sonix MSIC-75M S-12 polymer transducer, the Panametrics V3815 crystal, delay-line transducer, the Panametrics A334S-SU paintbrush transducer, the Krautkramer linear array and the Imperium DAV area array.

Figure 2:
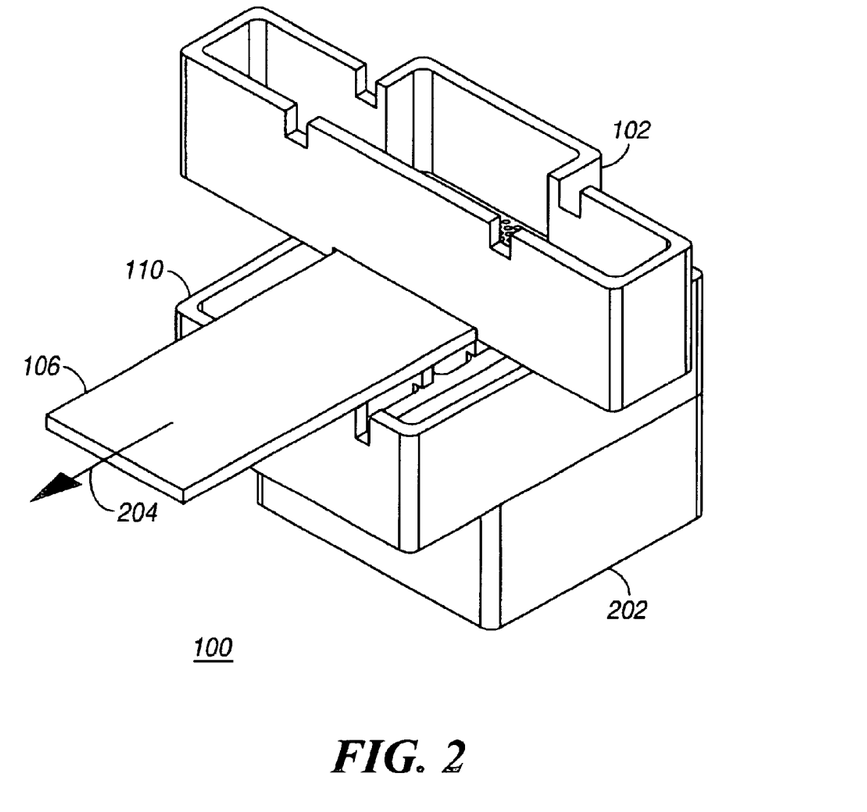
FIG. 2 is a further view of the ultrasonic test chamber shown in FIG. 1.

An assembled ultrasonic test chamber 100 is shown in FIG. 2. The upper chamber 102 is supported by a frame (not shown) so that the moveable plate or scan bar (104 in FIG. 1) is in close proximity to the upper surface of the parts in the tray of parts 106. The tray of parts 106 is moved in the direction of arrow 204 along a track, entering the right side of the chamber in the figure and exiting the left side. The tray may be propelled along the track by an arm connected to a screw drive, for example. The upper and lower chambers are kept filled with a coupling fluid. Fluid is added at rate sufficient to compensate for the fluid lost through openings in the upper and lower chambers. Spilled fluid may be collected in a reservoir 202 and used to the refill the chambers. The re-filling can be performed by a pump so that fluid is re-circulated from the reservoir to the upper and lower chambers. In this manner, the tray of parts may be maintained in a substantially horizontal position.

Figure 3:
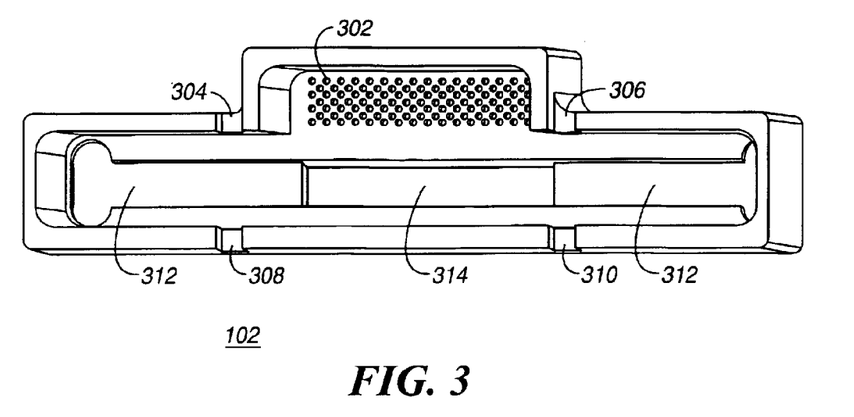
FIG. 3 is a diagrammatic representation of an upper chamber of an ultrasonic test chamber.

Fluid flow through the tray of parts is restricted, so fluid may be added to the tray from the upper chamber at a rate sufficient to maintain sufficient fluid in the tray to permit acoustic coupling of the ultrasonic beam to the top of the parts in the tray. If measurement of transmission through the part is not required, the lower chamber may be omitted or replaced with a fluid-capture tray. A more detailed view of the upper chamber 102 is shown in FIG. 3. The chamber is viewed from above. In use, the tray of parts first passes below a region of perforations or holes 302. In a further embodiment, the region 302 may contain a single slot. Region 302 is the de-bubbling region. Fluid is passed from below the parts and directed toward the underside of the parts so as to remove air bubbles. Excess fluid passes through the perforations or one or more slots 302 and enters the upper chamber. Additional fluid may be added to the upper chamber as required. The perforations or slots are sized so as prevent the parts from being dislodged by the fluid flow. Excess fluid may escape through one or more channels 304, 306, 308, 310, or through drain pipes (not shown). A track 312 is provided to guide the scanning bar 104. The scanning bar slides from left to right and right to left with the first transducer as it traverses the parts in the tray. The ultrasonic beam or transducer passes through opening 314. The parts in the tray are held in place by the scanning bar. In a further embodiment, the de-bubbling area and the scanning area may be separated.

Figure 4:
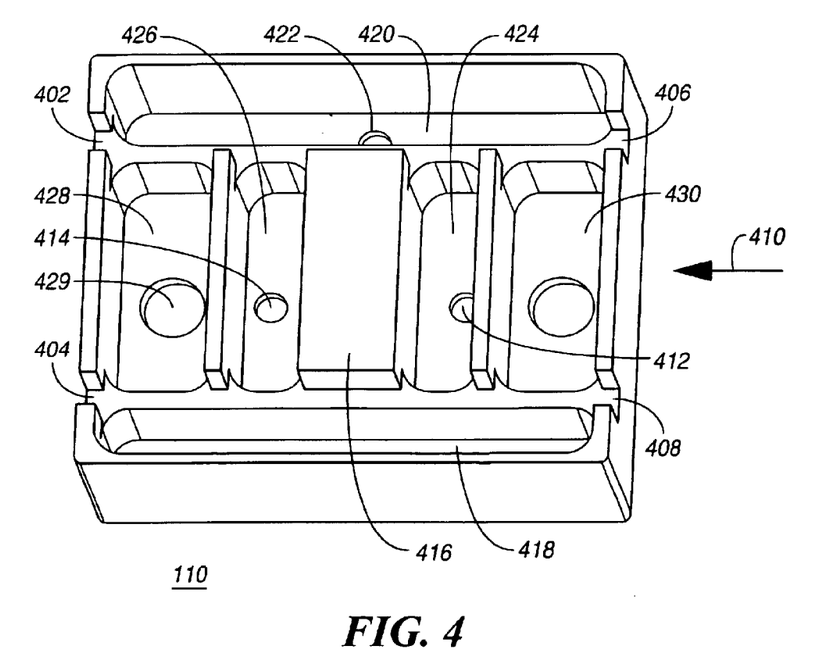
FIG. 4 is a diagrammatic representation of a lower chamber ultrasonic test chamber bottom.

A more detailed view of the lower chamber 110 is shown in FIG. 4. The chamber is viewed from above. In use, the tray of parts enters on the right of the figure, moving in the direction of arrow 410. The lower chamber is positioned below the tray of parts 106 (not shown). The tray of parts moves along a track. One rail of the track lies in the slot between openings 402 and 406, the other lies in the slot between opening 404 and 408. In the embodiment shown in FIG. 4, the lower tray is symmetric so that parts may enter from the left or the right. If parts enter from the left, the upper chamber is rotated through 180°. The following description assumes that trays enter from the right in the figure. Chamber 430 is a copy of chamber 428 and is included to permit reversal of the tray movement. It is not necessary. De-bubbling chamber 424 is positioned below the de-bubbling region (302) of the upper chamber. Fluid is injected into the de-bubbling chamber 424 through hole 412. The fluid may be injected at multiple locations. The injected fluid serves to dislodge air bubbles adhering to the underside of the parts in the tray. The tray then passes over raised region 416. Preferably the raised region is a substantially planar surface. This surface prevents the turbulence from the fluid in chamber 424 from reaching the scanning region, it also tends to reduce fluid flow, facilitating the ultrasonic coupling between the transducer and the parts in the tray. The scanning region may be above the raised region 416 or to the left of the raised region. If a second transducer is employed, it may be embedded in the raised region or positioned immediately to the left of the raised region. Drain chamber 426 is positioned after the scanning region. Fluid is drained from this region through opening 414. The region will typically contain both fluid and air, and will allow the underside of the parts to begin to dry. Fluid flows from the de-bubbling chamber 424 to the drain chamber 426, thereby maintaining a flow of fluid from right to left across the raised region 416. This flow, combined with the column of fluid above the parts being scanned, helps to keep the parts in place. Finally the tray of parts enters the drying region above chamber 428. Air suction may be applied at opening 429 to help hold the parts in place. The parts are then dried by an air knife, hot air, a brush or by wicking materials (or a combination thereof). The brush or wicking materials are attached to the top side of the lower chamber or to the support frame. Side chambers 418 and 420 collect fluid spilled from the sides of the center chambers (424 and 426) and contain drain holes (422 for example) to allow the spilled fluid to be captured in the reservoir.

In a further embodiment, the upper and lower chambers may be integrated, and height of the flat plate varied to accommodate trays of varying thickness.

Figure 5:
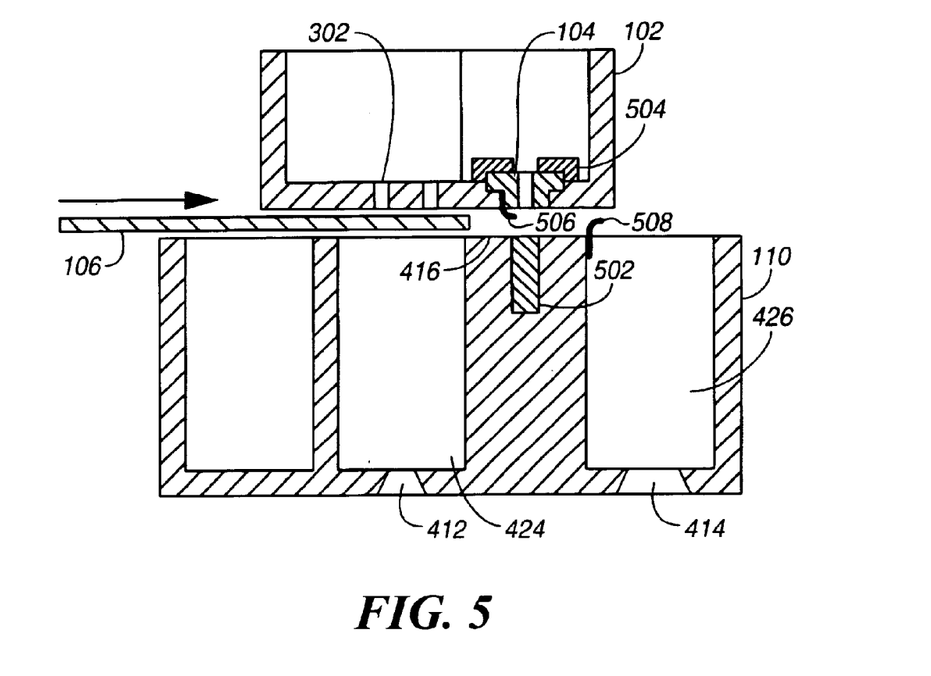
FIG. 5 is a cross sectional diagram of an ultrasonic test chamber in accordance with certain embodiments of the present invention.

FIG. 5 shows a cross-sectional diagram of an exemplary ultrasonic test chamber. A vertical cross-sectional along the axis of motion of the parts tray 106 is shown. The parts tray moves from left to right in the figure. The lower chamber 110 includes a de-bubbling chamber 424 with opening 412 to receive a flow of fluid. In this embodiment, a second transducer 502 is embedded in the raised region 416 to permit through-transmission measurements. The drying chamber 426 includes opening 414 where air suction may be applied to hold the parts in place while they are dried. The upper chamber 102 includes at least one opening 302 through which fluid from the de-bubbling chamber passes. The moving flat plate or scanning bar 104 includes an opening to accommodate the first transducer. A brace or bracket 504 may be used to prevent movement of the flat plate in directions other than the scan direction. Preferably the scan direction is in a horizontal plane perpendicular to the motion of the tray, although skewed scan directions may be used. A set of spring fingers 506 may be used to hold the parts in place while scanning is performed. The spring fingers 506 are attached to the upper chamber 102 and extend downwards and in the direction of motion of the tray. As the tray passes under the spring fingers they are displaced upwards and exert a downward spring force on the parts in the tray. A brush or wicking material 508 is attached to the lower chamber to remove water droplets from the bottom surface of the parts in the tray.

Figure 6:
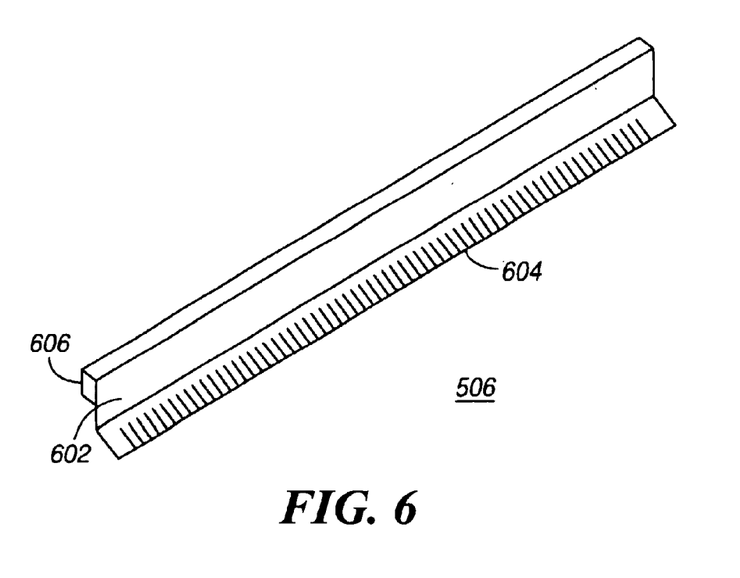
FIG. 6 is a diagrammatic representation of an array of spring fingers in accordance with certain embodiments of the present invention.

A more detailed view of the spring fingers 506 is shown in FIG. 6. In this embodiment, a sheet of metal 602 is bent to form an angle. Slots 604 are formed in the metal on one side of the fold. The material between the slots forms the spring fingers. Projection 606 may be included to facilitate attachment of the set of the spring fingers to the upper chamber.

A more detailed description of the operation is given below, together with some alternative embodiments.

De-Bubbling Area

The de-bubbling area is where the parts in the carriers are wetted and air bubbles are removed. Several aspects of the de-bubbling area are now described.

Side Fluid Penetration

The test chamber of the present invention is partially filled with a coupling fluid, such as water, to facilitate coupling of the ultrasonic beam to the part under test. The test chamber has one or more openings in the sides, below the level of the fluid, to allow a parts carrier to passing into the chamber. In one embodiment, this opening is the gap between the upper and lower chambers. Since fluid will leak from the opening, additional fluid is passed into the chamber to maintain the fluid level. Preferably, the fluid leaking from the one or more openings is collected and returned to the chamber. The carrier does not have to be raised or lowered, so the system is compatible with production line configurations and handling equipment Water Jet To remove any air bubbles adhering to the parts, a stream of water or other fluid is forced across the parts. Preferably, the flow of water is from bottom to top because that is the directions the air bubbles will float when separated from the part or carrier.

Perforated or Slotted Cover

In the case where the water jet is flowing upward, the water will tend to dislodge the parts from the carrier. A perforated or slotted cover is used to hold the parts in the carrier. The holes are large enough to let water and air bubbles pass but small enough so that parts can not pass or be dislodged.

Scanning Station

The scanning station is where wetted and bubble free parts are ultrasonically scanned. The ultrasonic transducer is moved across the parts at high speed in close proximity to the parts. The result is a motion in the fluid that tends to move the parts in the carriers or dislodge them from the carrier. For though-transmission (TT) tests, separate transducers or arrays of transducers are used above and below the carrier. The scanning station of the present invention uses one or more of the following approaches to hold the parts in the holder:

Carriers with Retaining Clips

In a first embodiment of the present invention, a carrier with retaining clips is used to prevent the parts in the carriers from being dislodged. In some areas of the semiconductor part manufacturing process, it is advantageous to hold the parts in a carrier with a retaining clip. For example, the Auer Company manufactures metal carriers commonly referred to as boats that have retaining clips (For example, Auer part number A27150-001 manufactured in 9/00 per drawings 110892 Rev. B). Boats can be used in curing ovens and other stages of semiconductor manufacturing. Current practice is to remove the parts from these "boats" and place them in JEDEC trays before scanning ultrasonically. By scanning the parts in the "boats" the parts do not have to be moved to another carrier and the parts are held in place during the ultrasonic scan.

High Pressure Above Carrier

In one embodiment of the invention, fluid is added to the parts carrier from above. The fluid is added at one or more positions away from the scanning area, so that fluid flow does not tend to dislodge the parts. Furthermore, since flow through the parts carrier is restricted, the static fluid pressure above the parts is higher than the pressure below the parts. This results in a net downward force acting to hold parts in the part carrier. Thus, the coupling fluid tends to hold the parts in place rather than to dislodge them.

Low Pressure Under Carrier

Because any motion in the fluid (caused for example by transducer movement) around the parts may tend to move the part in the holder during the scan (which results in a blurred ultrasonic image) or dislodge the part entirely from the holder, it is desirable to have some type of force holding the parts in to holder. Since materials other than the coupling fluid (typically deionized water) will have a different acoustic impedance and degrade the ultrasonic image, it is desirable for this force to be applied via the coupling fluid. In one embodiment of the invention a fluid flow is maintained below the carrier. This results in a net downward force on the parts that will tend to hold the parts in the carrier. The flow is maintained across the raised region of the lower chamber.

Figure 7:
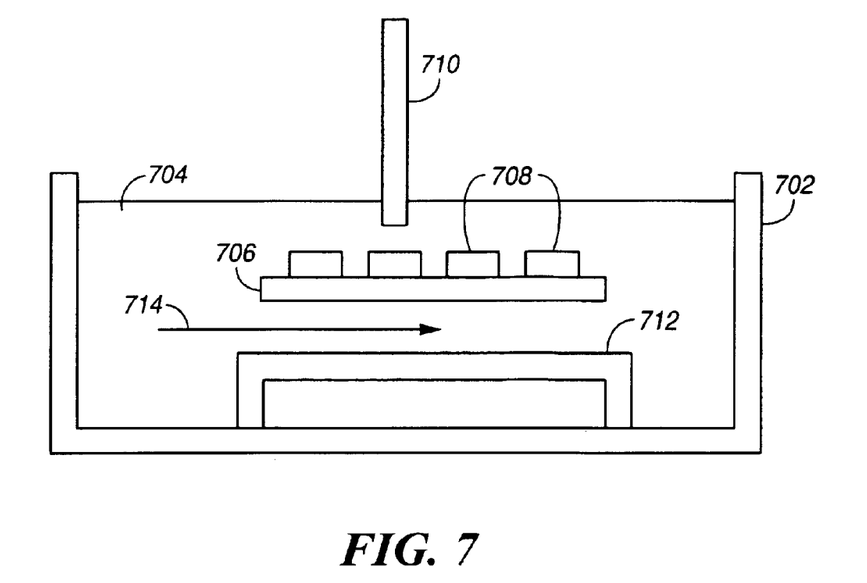
FIG. 7 is a cross sectional diagram of an ultrasonic test chamber in accordance with further embodiments of the present invention.

FIG. 7 is a simplified cross-sectional diagram of an ultrasonic test chamber in accordance with a further embodiment of the present invention. In this embodiment, the scanning station comprises a tank 702 containing coupling fluid 704. A tray 706 supports a number of objects 708. Typically, the objects are loosely held. An ultrasonic transducer 710 is used to scan the objects. A second transducer (not shown) may be used to sense the ultrasound transmitted through the objects. The holder or tray 706 is held above a surface 712. Preferably, the surface is flat in the direction of the scan line of the ultrasonic transducer 710, but may be curved in the other direction to facilitate fluid flow. A flow of coupling fluid is generated in the direction of the arrow 714, between the surface 712 and the underside of the tray 706. This flow produces a lower pressure beneath the tray. The pressure differential across the object in tray results in a net downward force on the object and holds the object in the tray, and prevents it from being dislodged by turbulence produced by motion of the ultrasonic transducer or the tray. The flow may be generated, for example, by fluid jets acting on one side of the tray or by suction acting on one side of the tray.

Figure 8:
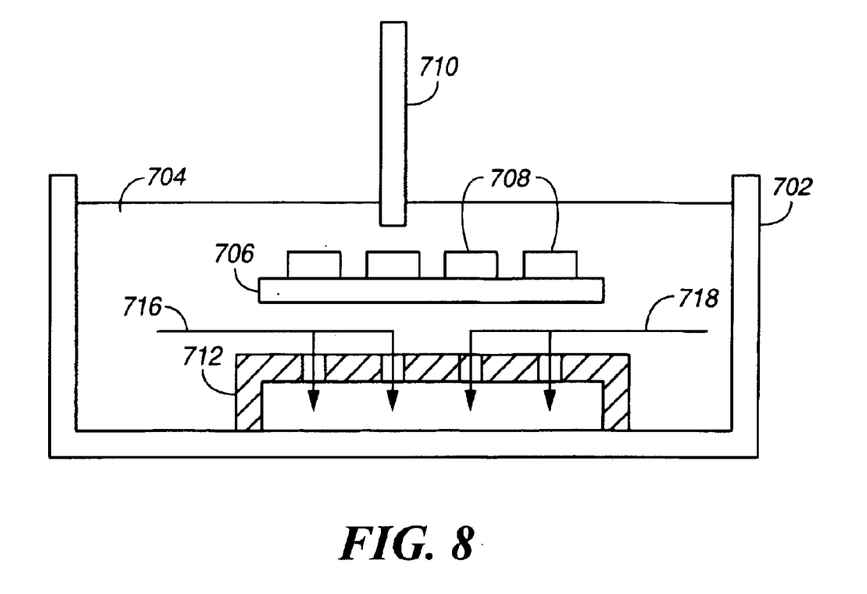
FIG. 8 is a cross sectional diagram of an ultrasonic test chamber in accordance with still further embodiments of the present invention.

FIG. 8 is a simplified cross-sectional diagram of a ultrasonic test chamber in accordance with a still further embodiment of the present invention. In this embodiment, the scanning station comprises a tank 702 containing coupling fluid 704. A tray 706 supports a number of objects 708. Typically, the objects are loosely held. An ultrasonic transducer 710 is used to scan the objects. A second transducer (not shown) may be used to sense the ultrasound transmitted through the objects. The tray 706 is held above a surface 712. Preferably, the surface is flat in the direction of the scan line of the ultrasonic transducer 710. A flow of coupling fluid is generated in the direction of the arrows 716 and 718, between the surface 712 and the underside of the tray 706. The flow is produced by drawing fluid, from beneath the surface 712, through one or more holes in the surface. This flow produces a lower pressure beneath the tray. The pressure differential across the object in tray results in a net downward force on the object and holds the object in the tray, preventing it from being dislodged by turbulence produced by motion of the ultrasonic transducer or the tray. Other methods for producing a suitable fluid flow will be apparent to those of ordinary skill in the art.

Retaining Strip

In a further embodiment, where additional force is required to hold the parts in the holder at the scanning station, a retaining strip is used. The retaining strip is comprised of a continuous strip or a series of fingers made out of a spring-like material that applies a slight downward pressure to the top of the parts. The fingers are positioned so that they do not cover the parts at the scan line. Two rows of retaining strips, one prior to and one after the scanning line are used.

Scanning Bar (Moving Cover)

In a further embodiment, a flat plate or bar mounted flush with the bottom of the transducer is used to prevent the parts in the holders from being dislodged. The flat plate, referred to as a scanning bar, acts as a barrier between the fluid around the transducer that is disturbed during motion and the fluid surrounding the parts in the holder. This prevents the disturbed fluid from tending to affect the position of the parts. If the scanning bar is kept in close proximity to the top of the holder it will also insure that parts can not leave the holder in the scanning station. To keep the size and mass of the scanning bar small, the scanning bar can be integrated with a stationary cover to insure that the parts cannot leave the holder while in the scanning station.

The above techniques, namely scanning bar, retaining strip, high-pressure and low pressure, can be used in any and all possible combinations.

Fixed Through-Transmission Transducer

Through-transmission tests typically require a transmitter on one side of the part and a receiver on the other side. Typically, both of these transducers will move together at the same rate and directions. By using a single element or array transducer for either the UT transmitter or receiver, only one of the two transducers will be in motion thereby reducing the disturbance to the fluid around the parts and simplifying the mechanics required to implement a system. In the preferred embodiment, the fixed transducer is located below the holder so that the moving transducer can be in closer proximity to the parts which is currently a requirement for the high frequency scans.

Fixed Array (Linear and Area)

If any/all of the ultrasonic transducers required are linear or area arrays the speed required can be reduced thereby reducing the tendency for the parts to move or be dislodged from the holder. In the preferred embodiment, the transducers will completely cover the width of a tray and will not be required to move at all. The array could be integrated with a top or bottom cover plate. The array could also be used in conjunction with a fixed through-transmission transducer.

Dryer

After the ultrasonic scanning of the parts in the holder is completed, it is desirable to remove the coupling fluid from the parts to prevent the fluid from affecting the quality or appearance (i.e. water spots) of the parts. The dryer of the present invention includes one or more of the following:

Gas Stream

A gas stream can be used to dry any residual coupling fluid from the parts. Typically compressed and/or heated air is directed across the parts. By using a vacuum or suction from beneath the holder, drying gas will still flow across the parts but it will tend to hold the parts in the holder rather than dislodge them. Additionally, an air-knife can be used to blow residual fluid from the upper surface of the parts.

Wicking Material

If any liquid residue is left on parts, a wicking material may be placed in contact with the part to remove the moisture.

Brush

If any liquid residue is left on parts, the parts may be passed under a brush, so that bristles of the brush contact with the part and remove the moisture. Preferably, the brush contacts the lower surface of the part.

While the invention has been particularly shown and described with reference to exemplary embodiments, it will be understood by those skilled in the art that various changes in form and detail may be made therein without departing from the spirit and scope of the invention. In addition, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

What is claimed is:

1. A method for ultrasonic scanning of an object supported by an object holder in a scanning station, the scanning station comprising an upper chamber and housing an ultrasonic transducer with an ultrasound emitting surface, the method comprising:

moving the object beneath the upper chamber;

insonifying the object with ultrasound from the ultrasonic transducer;

supplying a coupling fluid to the upper chamber so that coupling fluid flows through one or more holes in the bottom of the upper chamber onto the object, thereby filling the space between the ultrasound emitting surface of the ultrasonic transducer and the object; and sensing ultrasound reflected from or transmitted through the object, wherein the static pressure of the coupling fluid exerts a downward force on the object tending to hold the object in the object holder.

2. A method in accordance with claim 1, wherein the object is a part and the object holder is a parts holder supporting a plurality of parts.

3. A method in accordance with claim 2, wherein the parts holder has holes therein to allow the coupling fluid to pass from the upper chamber through parts holder.

4. A method in accordance with claim 1, wherein the scanning station further comprises a lower chamber, further comprising:

collecting the coupling fluid in the lower chamber; and recirculating the coupling fluid to the upper chamber.

5. A method in accordance with claim 4, further comprising adjusting the distance between the upper and lower chambers in accordance with the thickness of the object.

6. A method in accordance with claim 4, wherein moving the object comprises moving the object in a first horizontal direction along a substantially horizontal track attached to the lower chamber.

7. A method in accordance with claim 6, further comprising moving the ultrasonic transducer in a second horizontal direction along a slot in the bottom of the upper chamber.

8. A method in accordance with claim 4, further comprising moving the ultrasonic transducer in a horizontal plane across the object holder.

9. A method in accordance with claim 4, wherein in the lower chamber incorporates a raised surface, further comprising generating reduced fluid pressure in the coupling fluid between the raised surface of the lower chamber and the object.

10. A method in accordance with claim 9, wherein the reduced pressure is generated by a flow of coupling fluid between the raised surface of the lower chamber and the object.

11. A method in accordance with claim 10, further comprising:

flowing the coupling fluid from a de-bubbling chamber between the raised surface of the lower chamber and the object holder.

12. A method in accordance with claim 1, further comprising moving a horizontal scan bar with the ultrasonic transducer, thereby reducing turbulence in the coupling fluid in the space between the ultrasound emitting surface of the ultrasonic transducer and the object in the object holder.

13. A method in accordance with claim 1, further comprising drying the object in the object holder using at least one of an air-knife, a wicking material and a flow of warm air.

14. A method in accordance with claim 13, wherein the drying further comprises:

reducing the air pressure below the object holder so as to prevent the object from being dislodged from the object holder.

15. A method in accordance with claim 13, further comprising:
reducing the air pressure below the object holder so as to prevent the object from being dislodged from the object holder; and
removing fluid from the object in the object holder using a brush.

16. A method for removing bubbles from the surface of an object in an object holder prior to ultrasonic scanning, the method comprising:
supplying a flow of fluid to an upper de-bubbling chamber so that fluid flows through one or more holes in the bottom of the upper de-bubbling chamber; and
moving the object beneath the upper de-bubbling chamber through the flow of fluid from the one or more holes in the bottom of the upper de-bubbling chamber,
wherein the static pressure of the fluid exerts a downward force on the object tending to hold the object in the object holder.

17. A method for removing bubbles from the surface of an object in an object holder prior to ultrasonic scanning of the object, the method comprising
moving the object between the upper surface of a lower de-bubbling chamber and a cover containing at least one aperture large enough to allow fluid and bubbles to pass but small enough to prevent passage of the object; and
supplying a flow of fluid to a lower de-bubbling chamber so that fluid flows upwards past the object through the at least one aperture in the cover.

18. A method for ultrasonic inspection of an object in an object holder holding one or more objects, the method comprising:
immersing the object and the object holder in a tank containing coupling fluid;
generating a flow of fluid in the tank beneath the object holder, whereby a suction pressure is produced tending to hold the one or more objects in the object holder;
the de-bubbling station comprising:
an upper de-bubbling chamber having at least one opening in its bottom surface, the at least one opening being sized so that the object cannot pass through; and
a lower de-bubbling chamber located below the upper de-bubbling chamber and spaced therefrom to allow the object to pass between the upper de-bubbling chamber and the lower de-bubbling chamber;
wherein the lower de-bubbling chamber is operable to supply a flow of fluid directed towards the object and the upper chamber is operable to receive at least some of the flow of fluid through the at least one opening; and
the scanning station comprising:
a holder support structure for supporting the object holder;
an upper scanning station chamber positioned above the holder support structure; and
a first ultrasonic transducer located within the upper scanning
insonifying the object with ultrasound from an ultrasonic transducer; and
sensing ultrasound reflected from or transmitted through the object.

19. A method in accordance with claim 18, wherein the flow of fluid is generated by at least one fluid jet directed at one side of the object holder.

20. A method in accordance with claim 18, wherein the flow of fluid is generated by creating a suction acting at one or more sides of the object holder.

21. A method in accordance with claim 18, wherein the flow of fluid is a generated by creating drawing fluid out of at least one hole in the tank beneath the object holder.

22. A method in accordance with claim 18, wherein the object holder is supported above a raised surface having at least one hole therein, and wherein the flow of fluid is a generated by drawing fluid through the at least one hole in the raised surface.

23. An ultrasonic test chamber for use in inspecting an object in an object holder, the ultrasonic test chamber comprising at least one of a de-bubbling station and a scanning station,
the de-bubbling station comprising:
an upper de-bubbling chamber having at least one opening in its bottom surface, the at least one opening being sized so that the object cannot pass through; and
a lower de-bubbling chamber located below the upper de-bubbling chamber and spaced therefrom to allow the object to pass between the upper de-bubbling chamber and the lower de-bubbling chamber;
wherein the lower de-bubbling chamber is operable to supply a flow of fluid directed towards the object and the upper chamber is operable to receive at least some of the flow of the fluid through the at least one opening; and
the scanning station comprising:
a holder support structure for supporting the object holder;
an upper scanning station chamber positioned above the holder support structure; and
a first ultrasonic transducer located within the upper scanning station chamber;
wherein the upper scanning station chamber is operable to receive and dispense coupling fluid at a rate sufficient to provide fluid coupling between the ultrasonic transducer and the object and to provide a static fluid pressure acting on the object and tending to retain the object in the object holder.

24. An ultrasonic test chamber in accordance with claim 23, further comprising a scanning bar extended in the direction of the scanning path and adapted to move with the first ultrasonic transducer.

25. An ultrasonic test chamber in accordance with claim 24, wherein the first ultrasonic transducer has an ultrasound emitting surface and is located in an orifice in the scanning bar such that the ultrasound emitting surface is approximately in same plane as the underside of the scanning bar.

26. An ultrasonic test chamber in accordance with claim 24, wherein first the ultrasonic transducer is moveable in a vertical direction relative to the scanning bar to allow focusing of the ultrasound.

27. An ultrasonic test chamber in accordance with claim 23, further comprising a line of spring fingers attached to one of the upper de-bubbling chamber and the upper scanning station chamber, the spring fingers operable to exert a downward force on the object.

28. An ultrasonic test chamber in accordance with claim 23, wherein the first transducer is moveable in a scanning path.

29. An ultrasonic test chamber in accordance with claim 23, wherein the first transducer is fixed in the upper scanning station chamber and comprises at least one of a transducer with an array of elements and an array of transducers.

30. An ultrasonic test chamber in accordance with claim 23, wherein the object is a part of a plurality of parts and the object holder is a parts tray.

31. An ultrasonic test chamber in accordance with claim 23, further comprising:
a lower scanning station chamber located below the upper scanning station chamber and spaced from it to allow the object to pass between the upper scanning station chamber and the lower scanning station chamber.

32. An ultrasonic test chamber in accordance with claim 31, wherein the first ultrasonic transducer is moveable in a scanning path and wherein the lower scanning station chamber comprises a raised surface located beneath the scanning path of the first ultrasonic transducer.

33. An ultrasonic test chamber in accordance with claim 31, further comprising a second ultrasonic transducer incorporated in the raised surface of the lower scanning station chamber.

34. An ultrasonic test chamber in accordance with claim 33, wherein the second ultrasonic transducer comprises at least one of a transducer with an array of elements and an array of transducers.

35. An ultrasonic test chamber in accordance with claim 31, comprising both a de-bubbling station and a scanning station, wherein the lower de-bubbling chamber is in close proximity to the lower scanning station chamber, whereby fluid flows from the lower de-bubbling chamber between the object holder and the raised surface of the lower scanning station chamber.

36. An ultrasonic test chamber in accordance with claim 23, further comprising a dryer having a lower drying chamber positioned below the object holder, the lower drying chamber having an opening from which air is drawn to maintain suction in the lower drying chamber.

37. An ultrasonic test chamber in accordance with claim 36, wherein the dryer comprises at least one of an air knife, a hot air flow and a line of wicking material.

38. An ultrasonic test chamber in accordance with claim 36, wherein the dryer comprises a brush.

39. An ultrasonic test chamber in accordance with claim 23, wherein the de-bubbling station further comprises a brush operable to contact a surface of the object as it passes through the de-bubbling station.

40. An ultrasonic test chamber in accordance with claim 23, comprising both a de-bubbling station and a scanning station, wherein the upper de-bubbling chamber and the upper scanning station chamber are connected and form an integrated upper chamber.

41. An ultrasonic test chamber in accordance with claim 23, comprising both a de-bubbling station and a scanning station, wherein the lower de-bubbling chamber and the lower scanning station chamber are connected and form an integrated lower chamber.

42. An ultrasonic test chamber in accordance with claim 41, further comprising a track coupled to the integrated lower chamber, the track operable to support the object holder and move it through the ultrasonic test station.

43. A method for ultrasonic scanning of a semiconductor part disposed, with a plurality of other semiconductor parts, in respective compartments of a tray at a scanning station, wherein the scanning station comprises an ultrasonic transducer, the method comprising:
moving the semiconductor part beneath the ultrasonic transducer;
insonifying the semiconductor part with an ultrasound signal from the ultrasonic transducer;
supplying a coupling fluid to the semiconductor part simultaneously with insonifying semiconductor part; and
generating a flow of fluid, so that the fluid flows beneath the semiconductor part to produce a low pressure tending to hold the semiconductor part in a desired position in the tray during insonifying the semiconductor part.

44. The method of claim 43, wherein generating a flow of fluid beneath the semiconductor part comprises generating a flow of the coupling fluid beneath the semiconductor part.

45. A method for ultrasonic scanning of a semiconductor part disposed, with a plurality of other semiconductor parts, in respective compartments of a tray at a scanning station, wherein the scanning station comprises an ultrasonic transducer, the method comprising:
moving the semiconductor part relative to the ultrasonic transducer;
insonifying the semiconductor part with an ultrasound signal from the ultrasonic transducer;
supplying a coupling fluid to the semiconductor part simultaneously with insonifying semiconductor part; and
generating a flow of fluid, so that the fluid flows beneath the semiconductor part to produce a low pressure tending to hold the semiconductor part in a desired position in the tray during insonifying the semiconductor part.

46. The method of claim 45, wherein moving the semiconductor part relative to the ultrasonic transducer further comprises moving the semiconductor part in the tray beneath the ultrasonic transducer.

47. The method of claim 45, wherein moving the semiconductor part relative to the ultrasonic transducer further comprises moving the ultrasonic transducer across the semiconductor part in the tray beneath the ultrasonic transducer.

48. A method for ultrasonic scanning of a semiconductor part disposed, with a plurality of other semiconductor parts, in respective compartments of a tray at a scanning station, wherein the scanning station comprises an ultrasonic transducer, the method comprising:
moving the semiconductor part beneath the ultrasonic transducer;
insonifying the semiconductor part with an ultrasound signal from the ultrasonic transducer;
supplying a coupling fluid to the semiconductor part simultaneously with insonifying semiconductor part; and
generating a flow of fluid, so that the fluid flows beneath the semiconductor part to produce a pressure differential between a lower pressure produced under the semiconductor part and a higher pressure on top of the part tending to hold the semiconductor part in a desired position in the tray during insonifying of the semiconductor part.

* * * * *